United States Patent [19]

Sache et al.

[11] 4,239,754

[45] Dec. 16, 1980

[54] LIPOSOMES CONTAINING HEPARIN AND A PROCESS FOR OBTAINING THEM

[75] Inventors: Edgar Sache, Bures-sur-Yvette; Henri Bertrand, Chatillon-sur-Bagneux, both of France

[73] Assignee: Choay, S.A., Paris, France

[21] Appl. No.: 845,106

[22] Filed: Oct. 25, 1977

[30] Foreign Application Priority Data

Oct. 23, 1976 [GB] United Kingdom ............... 44132/76
Aug. 16, 1977 [GB] United Kingdom ............... 34410/77

[51] Int. Cl.³ ............................................. A01N 43/16
[52] U.S. Cl. ..................................... 424/183; 424/180; 536/21
[58] Field of Search ....................... 424/180, 183, 315; 536/21

[56] References Cited

U.S. PATENT DOCUMENTS

| | | | |
|---|---|---|---|
| 2,055,083 | 9/1936 | Klein et al. | 424/180 |
| 3,395,222 | 7/1968 | Colescott et al. | 424/106 |
| 4,053,585 | 10/1977 | Allison et al. | 424/92 |

OTHER PUBLICATIONS

Chemical Abstracts, vol. 75, (1971), p. 58814h.
Chemical Abstracts, vol. 84, (1976), p. 53732f.

Primary Examiner—Johnnie R. Brown
Assistant Examiner—Blondel Hazel
Attorney, Agent, or Firm—Weiser, Stapler & Spivak

[57] ABSTRACT

Heparin-based preparations wherein heparin is retained in or on liposomes.

The lipids of said liposomes are preferably phospholipids comprising acyl chains derived from non saturated fatty acids, advantageously essential acids.

These heparin-liposomes preparations have heparinic activity when administered in vivo by the oral route and a delayed-type action.

2 Claims, No Drawings

LIPOSOMES CONTAINING HEPARIN AND A PROCESS FOR OBTAINING THEM

This invention relates to new pharmaceutical compositions containing heparin and to a process for obtaining such compositions. It is further concerned with such compositions capable of being administered not only by the routes used heretofore with conventional heparin compositions, but also by other routes.

Heparin is well known and widely used as a medicament or drug because of its remarkable anti-coagulating properties. However, heretofore it has not been practical to administer heparin to patients by other than a parenteral route. Continuous perfusion or intravenous or subcutaneous injections are the methods of administration usually employed.

In addition, the period of activity of the heparin doses administered in conventional compositions are generally—more particularly when administered intravenously—quite short, which makes it necessary to repeat quite often the administration, particularly injection, at least twice daily.

It is known that investigations have already been undertaken with a view to producing heparin preparations which either can be administered by other than parenteral route and especially by oral route, or where administration is by parenteral route, have prolonged periods of activity enabling the frequency of injections to be reduced. However, until now the investigations have been unsuccessful in finding a means of administering heparin which permits long-term treatment with more prolonged activity than those conventionally used.

This invention seeks to remedy, at least in part, to these disadvantages of conventional compositions.

More particularly, the object of the invention is to provide heparin-based preparations, the anticoagulant activity of which is capable of being brought to evidence at least in part, even when administered by the oral route.

Another object of the invention is to provide such preparations of heparin which, when administered by a parental route, have prolonged durations of action.

The preparation of the invention consists essentially of liposomes with heparine retained therein or thereon.

The invention further relates to dispersions of liposomes of that type in a liquid, particularly an aqueous vehicle. It also relates to pharmaceutical compositions containing said preparation or dispersions associated whenever necessary to a pharmaceutical vehicle enabling its administration.

Liposomes prepared from phospholipids, or from certain other lipid substances or hydrophobic fatty materials have already been described. The liposomes are constituted by hydrated lipid crystals, generally mono- or multi layered (or uni- or multi- lamellar) dispersed or disperable in an aqueous medium, with a part of the aqueous medium from which the crystals were produced being trapped in the vesicles formed as a result of the capacity of their lipids or fatty materials to undergo "swelling" in aqueous medium, especially under the effect of an agitation or of ultra-sonic radiation. These liposomes can also be described as being formed of one or a series of concentric bi-layers of the lipids, alternating with aqueous compartments. When the aqueous solution from which the liposomes were formed is or contains a solution of heparin, then a part of this heparin solution is retained by and in the interstices of the liposomes to form the compositions of this invention.

It has been found that such liposomes—prepared from physiologically acceptable lipids and formed within an aqueous solution of heparin—tend to produce in vivo certain biological effects characteristic of anticoagulating activity, and other usual activities of heparin when administered to subjects by oral or rectal route.

It has further been found that injectable dispersions formed with the preparations according to the invention are capable, in relation with their liquid contents, of inducing a delayed-type action upon their administration by the intravenous route.

The invention also provides a process for preparing liposomes retaining heparin, which process comprises subjecting a dispersion of physiologically acceptable lipids of the type capable of forming liposomes, preferably phospholipids, in a solution of heparin, preferably an aqueous one, to stirring or preferably to ultrasonic action (or sonication) until liposomes are formed which retain a part at least of the heparin initially contained in the aqueous solution.

The heparin used in this invention may, particularly, by any heparin useful in therapy. It can be used for instance in its acidic form or in the form of a salt formed with one or more metallic cations, such as sodium, calcium or magnesium. Any other type of heparin preparation suitable in therapy can be used.

For the sole purpose of examplifying types of heparin which can be used with advantage, it being understood that such indications should not be construed as an intent of limiting the scope of the present invention, it might be stated that heparins having molecular weights ranging from about 6000 to about 30,000 and having titers from about 150 to about 250 international units per mg (iu/mg) of heparin can be used with advantage. Such heparins, which comprise a large proportion of heparin species having molecular weights ranging from 10,000 to 15,000, and having a titer within the above range, have been used in the examples which will be described hereafter.

Obviously other heparin species, particularly those having molecular weights either above or below to either the upper or lower limits respectively of the range indicated above by way of example can be resorted to for preparing the liposomes according to the invention.

Concerning the lipids, it should be stated that any non toxic physiologically acceptable and metabolizable lipid, capable of forming liposomes, may be suitably used for carrying out the invention.

Phospholipids form an important class of said suitable lipids, more particularly (though non exclusively) the phospholipids having the formula

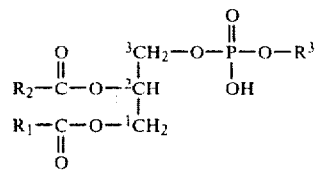

wherein $R_1$ and $R_2$ are derived from fatty acids, for instance those which comprise from 14 to 22, and preferably 18 and 20 carbon atoms and $R_3$ is part of an ester group, which in preferred instances is that which results from the esterification of the phosphoryl group of said phospholipid, by an amino-alcohol such as choline (2-hydroxyethyltrimethyl-ammonium hydroxide), ethanol-amine, serine, etc, . . . or by a sugar derivative comprising an ol function, such as inositol for instance. Other lipids more or less closely related to phospholipids and capable of forming liposomes, are also suitable for the invention. Among these one should cite, in a non limitative manner, particularly plasmalogens, gangliosides, sphingolipids, phosphoglycerides, phosphonolipids (particularly those which differ from the phospholipids of the above formula in that a —$CH_2$—$CH_2$—$NH_3$+ group is substituted for the —$OR_3$ group. ("LIPID BIOCHEMISTRY, An introduction" M. I. GURR and A. T. JAMES, 2nd edition, 1975, Chapman and Hall, London).

Other examples of useful lipids are those formed
of fatty acids comprising long non-saturated hydrocarbon chains, such as those designated as "ufasomes" and described by GEBICKI and HICKS; Chemistry and Physics of Lipids, 1976, Vol. 16, pages 142-160, or
of monoacylated compounds, comprising chains derived of fatty acids having eight or more carbon atoms as well as non toxic anionic and cationic pharmaceutically acceptable detergents, all of the type disclosed by W. R. HARGREAVES and D. W. DEAMER, "CONFERENCE ON LIPOSOMES AND THEIR USES IN BIOLOGY AND MEDECINE", Sept. 14-16, 1977, New-York Academy of Sciences, etc. . . .

Preferred classes of lipids, among which phospholipids, for use in the present invention, are those which comprise non-saturated fatty acid chains, such as those which comprise from 18 and 20 carbon atoms, and at least one non-saturated bond. Examples of these non saturated acids are oleic acid, or, even more preferably, the so-called "essential fatty acids", that is principally either linoleic acid or linolenic acid. Particularly, preferred phospholipids are those wherein at least one of the two above $R_1$ and $R_2$ groups are derived from at least one of the above said "essential fatty acids".

Representative phospholipids of this preferred class are the phosphatidylcholines of which at least one of the fatty acyl group is from a non-saturated fatty acid, preferably one of the said "essential acids". An example of such preferred phospholipids is 1,2-dilinoleyl-phosphatidylcholine.

More generally, reference can be made, for the selection of adequate phospholipids, to "PHOSPHATIDYLCHOLINES-BIOCHEMICAL AND CLINICAL ASPECTS OF ESSENTIAL PHOSPHOLIPIDS" by H. PEETERS—Springer Verlag, Berlin-Heidelberg—New-York, 1976.

Particularly suitable phospholipids compositions of this type are commercially available. Among these one may cite those known in the trade as, for example, V-E (Sigma) egg yolk phospholipids, or the natural "essential phospholipid" compositions formed or phosphatidylcholines esterified by fatty acids, a major proportion of which comprises mono- or preferably poly-unsaturated bonds, particularly 1,2. diacyl-sn-glycero-3-phosphorylcholines of mostly unsaturated fatty acids such as those which are extracted from soybean-seeds, such as the so-called EPL phospholipid composition manufactured by NATTERMAN (Germany).

The heparin-containing liposome preparations so obtained have most interesting biological properties, particularly induce anti-coagulant properties in vivo, even when administered orally. They also induce a delayed-type anticoagulant action.

These heparin-containing-liposome preparations which are formed starting from lipids, more particularly phospholipids having non saturated fatty-acid chains, advantageously derived of essential fatty acids, are of particular interest owing to the complementary therapeutical properties of said phospholipids themselves, which are of particular compatibility (often a particularly desirable one) with those of heparin.

More paticularly phosphatidylcholines are known to possess, among other valuable therapeutical properties, a protecting action against degenerative atheromatous processes or phenomena, to reduce capillar permeability and veinous tonicity, to prevent sludge formation in the capillary system and to decrease platelets hyperadhesivity and hyperaggregability.

They are further capable of acting favorably on hepatic lipidic excesses (hepatic steatosis) and, more generally, of restoring a proper balance between non-saturated and sturated fats, insofar as the latter are often in excess in the organism of those patients who suffer from vascular or cardiovascular diseases.

For carrying out the process according to the invention, conventional technology and equipment can be resorted to. This applies particularly to the use of sonication, which can be carried out for instance with the equipment comprising metallic probes introduced into the dispersion which is to be subjected to sonication. The ultimate nature and sizes of the phospholipidic vesicles will, as is well known, depend upon the time and intensity of sonication, the type of the lipids used, the ionic strength of the medium, the temperature, etc. As far as the technics are concerned, reference can, for instance, be had to chapter IV of METHODS IN CELL BIOLOGY edited by Dvaid M. Prescott, volume XIV, 1976, Academic Press, New-York, page 33.

Advantageously, the initial dispersion is obtained from a thin film of lipid formed in the vessel intended to contain the final product, this thin film preferably being obtained by introducing a solution of the appropriate lipids into the vessel and then evaporating the solvent therefrom. The heparin solution may then be introduced into the vessel whereby a dispersion of the lipids in the solution of heparin is formed, by stirring, which dispersion can then be subjected to ultrasonic radiation to obtain the above-indicated result.

In a first stage, there is formed a suspension of swollen liposomes having a milky aspect, the liposomes of which are then believed to be essentially formed of a series of concentric lipid bi-layers alternating with aqueous compartments in which heparin is retained.

The liposomes so obtained may be separated from the aqueous medium for example by centrifugation. The liposomes contained in the sediment may then be washed if desired so as to eliminate any active substance not incorporated into the liposomes. The liposomes may then be taken up in a buffer and stored, desirably in the cold and preferably at a temperature of +4° C. Liposomes stored in this manner are stable over prolonged periods of time.

It has however been fond that liposomes can be obtained which retain even greater amounts of heparin upon controlling and prolonging the conditions of stirring, particularly sonication, so as to provide smaller liposomes, particularly unilamellar vesicles within the starting aqueous solution of heparin.

This can be achieved upon prolonged sonication, if need be under higher electrical current-intensities than in the first instance.

Particularly, reliance can be made on the aspect of the suspension which is obtained after sonication to recognize whether the liposomes are essentially formed of the unilamellar vesicles or not. Instead of the milky suspension-aspect as formed by the multi-lamellar liposomes, the uni-lamellar liposomes give rise to slightly opalescent or merely transparent colloidal suspension.

The liposomes so formed can no longer be separated from the solution, by ultracentrifugation; it is no longer feasible to subject them to washing operations (which altogether would not appear as being necessary) owing to their small sizes (from about 250 to about 1000 Angstroms). They are however separable by gel filtration.

It has been found that under such conditions, liposomes can be obtained which retain from 500 to 2000 i.u. (international units) of heparin per ml of liposome preparation. It is here recalled that these amounts can be measured upon subjecting the heparin-containing-liposome preparation so obtained and separated from the medium in which they were formed, to the action of a detergent within an aqueous medium and assaying the heparin freed from the liposomes in the aqueous medium. Preferably the initial lipid composition also contains a stabilising agent, for instance cholesterol. If need be, an amphiphilic agent may be added within the initial lipid dispersion to cause the liposomes to be formed to also be charged electrically. Suitable agents include dicetyl-phosphate or phosphatidyl-serine if a negative charge is desired, or stearylamine if a positive charge is desired.

These amphiphilic agents can however also be dispensed with as this will appear from some of the following examples which will now be described for the purpose of further illustrating the invention, yet without limiting it in any manner whatsoever.

EXAMPLE 1

A lipid phase made up of the three components lecithin, cholesterol and dicetyl-phosphate in a molar ratio of 7:2:1, was prepared as follows. 26 mg of lecithin, 4.4 mg of cholesterol and 3.11 mg of dicetyl-phosphate were dissolved in 5 ml of chloroform. The solution obtained was evaporated to dryness in a round bottomed flask at a temperature at 37° C. After the chloroform had been evaporated off, the phospholipid constituents formed a thin film on the walls of the vessel used. From 30 to 50 mg of heparin were then dissolved in 5 ml of a 0.00 R M phosphate buffer at pH 7.2, and the solution obtained was introduced into the same vessel under nitrogen atmosphere.

The formed medium was left to stand for about 1 hour at room temperature, and the formed dispersion was then subjected to the action of ultrasonic radiation (sonication) for 10 seconds using a sonication apparatus of the type known under the trade mark ULTRA-SONIC, operating at 1.5 amperes, for 10 seconds. The probe of the sonication apparatus was made of standard stainless steel, but it could also be formed of other materials such as titanium. Further sonication for a period varying from 10 seconds to 20 minutes did not bring about any perceptible modification in the heparin content in the liposomes finally obtained, as measured in the test described hereinafter.

After sonication, the medium was left to stand for 1 hour at +4° C., and then centrifuged for 3 hours at 110,000 g.

The precipitate obtained was put back into suspension in the same phosphate buffer and centrifuged again for 3 hours at 110,000 g. The sample of an aliquot portion of the supernatant liquid was then found to be free from heparin.

The precipitate obtained was then resuspended in 0.3 ml of the phosphate buffer and the suspension obtained containing 9 i.u. of heparin stored in the cold, at a temperature of +4° C., for several months.

EXAMPLE 2

Liposomes containing heparin were made up by employing the same process as in Example 1, but starting with the following reactants:

lecithin (lecithin from egg yolk sold by the company SIGMA, type V): 26 mg (40 µmoles)
cholesterol: 4.4 mg (11.4 µmoles)

The liposomes thus obtained had a neutral charge.

EXAMPLE 3

Liposomes containing heparin were made up by employing the process as in Example 1, but starting with the following reactants:

lecithin: 26 mg (40 µmoles)
cholesterol: 4.4 mg (11.4 µmoles)
stearylamine (octade cylamine): 1.53 mg (5.7 µmoles)

These liposomes had a positive charge.

The effective entrapment by the liposomes of a certain amount of heparin was verified as follows:

0.1 ml of the liposome suspension was added to 1 ml of human plasma. The thrombin time was measured, whereby a total inertia of this suspension with respect to the thrombin time was established as compared to the results of tests carried out on a control formed of a dose of human plasma.

However it was found that when the same volume of the liposome suspension had previously been incubated for 30 minutes in the presence of an equal volume of a 1% solution of a detergent of the type known in the trade under the name TRITON X100 (Rohm & Haas), suitable for eliminating the lipid envelopes, the thrombin time was increased. The thrombin time, which is dependent upon a biologicalheparinaemia of a control plasma, was measured according to the heparinaemia evaluation method, by the testing of the thrombin period at variable concentration (RABY), Annales d'anesthesiologie francaise, volume 5, special issue 1954) and with modified standardisation (RABY, Coagulation IV, coagulation intravasculaire disséminée, Masson edition 1974, p. 188).

The measured amount was 1.8 iu for a volume of 0.1 ml of the suspension (liposomes+detergent). Liposomes alone formed in a solution not containing any heparin, did not show any activity in the above-mentioned test, whether they had been subjected to the action of detergent or not.

Test of biological properties in vivo of the liposomes containing heparin

The properties of the liposomes containing heparin were investigated on blood samples taken from male "Fauve de Bourgogne" rabbits, which had previously been administered by deep forced feeding using a gastro-duodenal catheter 3.6 ml per rabbit of the liposome suspensions in the buffer described hereinbefore (except for the rabbit considered in Table VI which received 10 ml, or a total of 180 iu, under the same experimental conditions). Blood samples were taken at different times after the forced feeding—after 30 minutes, 1 hour 30 minutes, 3 hours 30 minutes, 6 hours 30 minutes, 24 hours, 28 hours, 30 hours and 48 hours. Similar samples were taken from control rabbits, which had previously been forcibly fed only with water or with liposomes which did not contain heparin.

The samples which were collected in 5 ml tubes having water-repellant walls (of plastic material) and the calcium ion content of the samples was chelated by the addition of citrate ions. Under these conditions, the blood cellular and plasma contact factors, which are responsible for the initiation of the coagulatin process, were activated minimally, so that the different samples were no longer capable of coagulating spontaneously in the absence of ionised calcium.

The principle of the method used consisted of comparing the coagulation periods measured in the samples under test and in control samples, after recalcifying the contents of the tubes by adding calcium chloride, according to the thrombelastographic technique (TEG) described in "Biologie des hemorragies et des thromboses", G. RABY, Masson, Paris 1966, pages 186–188.

This technique takes advantage of the passage from the liquid state to the solid state of a blood preparation undergoing coagulation. The principle of the method consists of subjecting a vessel, into which the preparation to be studied had been introduced first, to an oscillating angular movement and to observe the coagulation effect on a cylinder suspended at the end of a torsion wire and dipping into the preparation. When coagulation begins, the plasma contained in the vessel imparts corresponding oscillatory movement to the cylinder.

The coagulation is timed from the instant (t=o) at which activation of the factors responsible for coagulation is induced by the addition of $Ca^{++}$ ions under the conditions indicated above.

In the following "r" is the induction time which precedes the effective beginning of coagulation;

"ma" is the maximum amplitude of the oscillations of the cylinder;

"k" is the interval in time from the moment when the cylinder begins to oscillate and the moment when the amplitude of the movement becomes equal to the amplitude (20 mm) obtained under the same conditions with a platelet-free plasma, the fibrinogen content of which is normal (3 to 4 g per thousand).

The "total coagulation time" of a preparation is constituted by the sum "r"+"k".

The kinetics of the coagulation are expressed by the parameters "r" and "r+k" and the dynamics of the coagulation by the maximum amplitude "ma" of the oscillations of the cylinder.

The results obtained are indicated in Tables I to VI which correspond to the tests having been carried out under the following conditions:

Table I: control rabbit forcibly fed with water only;
Table II: control rabbit forcibly fed with a suspension of liposomes free from heparin, in suspension in the same buffer:
Table III: rabbit forcibly fed with the suspension of liposomes containing heparin obtained in Example I above;
Table IV: rabbit forcibly fed with a suspension of liposomes containing heparin from another batch;
Table V: rabbit forcibly fed with a preparation of liposomes containing heparin from a mixture of several batches;
Table VI: rabbit forcibly fed with a larger amount of the preparation of liposomes (10 ml per rabbit).

In these tables are shown the measured values of the parameters "r", "k", "r+k", "ma" and TPI, the latter parameter being the thrombodynamic potential index expressed by the ratio (mxE)/k in which mxE=(100·ma)/(100−ma'), mxE=maximum elasticity. A "thromboelastogram" TEG can be recorded, which enables one to visually appreciate the phenomena induced.

TABLE I

Control (forcibly fed with H₂O)
TEG on whole blood

| | r | k | r + k | am | IPT | Observations |
|---|---|---|---|---|---|---|
| Before forcible feeding | 18 | 12 | 30 | 50 | 8.3 | |
| 30 mins after | 18 | 13 | 31 | 50 | 7.7 | |
| 1 h 30 mins after | 18 | 11 | 29 | 47 | 8 | |
| 3 h 30 mins after | 19 | 12 | 31 | 48 | 7.6 | |
| 6 h 30 mins after | Impraticable sample - coagulated blood | | | | | |
| 24 h after | 17 | 8 | 25 | 53 | 14 | Cardiac puncture |

TABLE II

Control liposomes alone
TEG on whole blood

| | r | k | r + k | am | IPT | Observations |
|---|---|---|---|---|---|---|
| Before forcible feeding | 17 | 10 | 27 | 60 | 15 | |
| 30 mins after | 13 | 8 | 21 | 69 | 27 | |
| 1 h 30 mins after | 20 | 9 | 29 | 71 | 27 | |
| 3 h 30 mins after | 11 | 11 | 22 | 69 | 20 | |
| 6 h 30 mins after | 18 | 7 | 25 | 61 | 22 | Difficult sample |
| 24 h after | 16 | 7 | 23 | 70 | 33 | Cardiac puncture |

TABLE III

Liposomes containing heparin
TEG on whole blood

| | r | k | r + k | am | IPT | Observations |
|---|---|---|---|---|---|---|
| Before forcible feeding | 9 | 6 | 15 | 70 | 38 | |
| 30 mn after | 21 | 15 | 36 | 52 | 7.2 | |
| 1 h 30 mins after | 19 | 10 | 29 | 53 | 11 | |
| 3 h 30 mins after | 7 | 6 | 13 | 67 | 33 | |
| 6 h 30 mins after | Impraticable sample - coagulated blood | | | | | |
| 24 h after | 22 | 10 | 32 | 60 | 15 | Cardiac puncture |

TABLE IV

Liposomes contaning heparin
TEG on whole blood

| | r | k | r + k | am | IPT | Observations |
|---|---|---|---|---|---|---|
| Before forcible feeding | 24 | 12 | 36 | 58 | 11.5 | |
| 30 mins after | 25 | 15 | 40 | 57 | 8.8 | |
| 1 h 30 mins after | 34 | 24 | 58 | 46 | 3.5 | |
| 3 h 30 mins after | 36 | 21 | 57 | 61 | 7.4 | |
| 6 h 30 mins after | 36 | 17 | 53 | 57 | 7.8 | |
| 28 h after | 50 | 21 | 71 | 50 | 4.7 | |

TABLE V

| | \multicolumn{5}{c|}{Liposomes containing heparin on whole blood} | |
|---|---|---|---|---|---|---|
| | r | k | r+k | am | IPT | Observations |
| before forcible feeding | 15 | 8 | 23 | 63 | 21 | |
| 30 mins after | 19 | 10 | 29 | 60 | 15 | |
| 1 h 30 mins. after | 26 | 14 | 40 | 57 | 9.5 | |
| 3 h 30 mins. after | 23 | 11 | 34 | 61 | 14.1 | |
| 6 h 30 mins. after | 6 | 7 | 13 | 53 | 16 | |
| 24 h after | 28 | 12 | 40 | 54 | 8.1 | |

TABLE VI

| | \multicolumn{5}{c|}{Liposomes containing heparin TEG on whole blood} | |
|---|---|---|---|---|---|---|
| | r | k | r+k | am | IPT | Observations |
| Before forcible feeding | 20 | 20 | 40 | 42,3 | 4,1 | |
| 30 mins after | 29,6 | 23,3 | 53 | 39,5 | 3.7 | |
| 1 h 30 mins after | 16 | 12,3 | 28.3 | 51 | 8.8 | Difficult sample |
| 3 h 30 mins after | 24,3 | 25 | 49.3 | 40,6 | 2,7 | Difficult sample |
| 6 h 30 mins after | 27.3 | 15.3 | 42,6 | 49 | 6.6 | Difficult sample |
| 24 h after | 39 | 33 | 72 | 43 | 3.5 | |
| 48 h after | 36.5 | 27 | 63.5 | 42.5 | 2.6 | |

The following observations can be made upon considering these results:

Forcibly feeding the rabbits, with water or with liposomes free from heparin, did not bring about significant modification in the parameters studied on the plasma of these rabbits (Tables I and II).

There was observed, however, in the case of the rabbits which had received liposomes containing heparin in their vesicles, a clear increase in the parameters "r", "k" and "r+k" (Tables III, IV, V and VI). The increase is at its maximum at the twenty-fourth hour, whereas the heparin administered according to standard techniques is eliminated, on average, within 4 hours following intravenous administration and within 12 hours following administration by subcutaneous route.

The effect on the parameter "r+k" was still observed 48 hours after administration, which indicates a very interesting delayed effect induced by the particular form of the composition of the invention under which the heparin was administered.

These results obtained with the composition of the invention always show effects in the same direction, namely an increase of the parameters "r", "k" and "r+k", from which it follows that the liposomes containing heparin administered "per os" have constantly an activity on coagulation kinetics.

Similar effects are constantly observed in rats too, upon their administering the above said heparin-containing liposomes.

Upon using the same sonication equipment, as in the previous examples, one can obtain smaller liposomes, more particularly unilamellar-liposomes, forming slightly opalescent and even almost transparent suspensions, for instance, upon subjecting to sonication a suspension of from 3.47 to 10.4 mg of lipids, such as phospholipids, and from 0.6 to 1.75 mg. cholesterol per ml of aqueous solution, containing advantageously from 5 to 15 mg of heparin (or from 900 to 2 700 i.u. of heparin) under a current intensity of from 3 to 8 amperes, over a period of from 30 minutes to 2 hours.

EXAMPLE IV

Several samples of lipids, each of which was formed of 104 mg of NATTERMAN-EPL-phospholipids and 17.6 mg of cholesterol, were dissolved in 5 ml of chloroform. The solutions were then evaporated under vacuum at 37° C. in a rotary evaporator, whereby thin lipidic films were formed on the walls of the corresponding glass vessels or flasks.

Different solutions containing from 50, 100 and 200 mg of heparin respectively dissolved in 5 ml of a 0.15 M NaCl solution and glass beads were added into the vessels. The solutions were subjected to stirring in VORTEX agitators under a nitrogen atmosphere, whereby the lipids which adhered to the glass walls of the vessels were detached therefrom and caused to form liposomes.

The contents of the vessels, in the form of milky suspensions were recovered; the liposomes which were still retained in the vessel were taken up by two successive volumes of a 0.15 NaCl solution and the recovered suspensions were then finally pooled to yield a final volume of 15 ml. The latter was left at rest for one hour at ambiant temperature, and then subjected to ultrasonication over varying periods of time ranging from 2 to 120 minutes (2; 5; 8; 10; 13; 25; 60; 90 and 120 minutes respectively) under current intensities varying from 1.5 to 8 amperes.

In all of these tests substantially translucid colloidal suspensions of liposomes were finally obtained.

EXAMPLE V

Particularly good results were obtained upon operating as follows:

104 mg of EPL-lipids (NATTERMAN) and 17.6 mg of cholesterol (SIGMA of USA) were dissolved in 5 ml of chloroform in a glass vessel and evaporated under vacuum at 37° C. A few glass beads and 5 ml of a 0.15 M NaCl solution containing 200 mg of heparin, with a titer of 182 i.u/mg, were added into the vessels. The contents of the latter were subjected to stirring under a nitrogen atmosphere in a VORTEX agitator until all of the phospholipids adhering to the walls of the glass vessel were in suspension in the heparin aqueous solution.

The lipid suspension was then recovered and the liposomes remaining in the vessel taken up twice by a 5 ml volume of a 0.15 M NaCl solution. After pooling of the suspensions the liposomes were then suspended in 15 ml of a 0.15 M NaCl solution. The suspended liposomes were left at rest for one hour and ultrasonically treated during 90 minutes at 4 amperes.

The suspension was then centrifuged at 10,000 g during 10 minutes. The suspension recovered was administered as such to rats in the tests referred to hereafter. Wistar male rats having average weight of 295 g (220-400 g) were fed with the liposome preparation of the foregoing example at different rates up to 15 000 i .u./kg of body weight, during varying periods of time from one day to nine days. Blood samples were taken after from 1 to 48 hours after the last feeding.

Under the experimental conditions used and despite individual variations which can be observed, it was found that several of the parameters conventionally used for determining the coagulability rates of a blood or plasma sample, i.e. thrombin time, Howell time, the cephalin-kaolin time as well as the thromboelastographic phenomena, were all modified towards a reduction of the coagulation capability of the plasma or blood samples tested. More particularly it was found that the administration of 15,000 i.u./kg of body weight resulted in the complete incoagulability of the blood of some of the rats which received that dose, whereas the feeding of controls with 25,000 i.u. per animal of an aqueous solution of the calcium salt of heparin or with a solution of 22,500 i.u. per animal of the sodium salt of heparin did not induce any significant effect on their blood coagulability under similar conditions.

In another test, Swiss mice were fed with 0.5 ml of the suspension of example 5, and controls received by the same route 0.5 ml either of water or of an aqueous solution containing 1,200 i.u. of the sodium salt of heparin.

One hour thereafter the mice were bled at the level of the tail.

Whereas in the controls which received water the bleeding times ranged from 2.5 to 12 minutes, and in those of the mice which had received the aqueous solution of the sodium salt of heparin from 3 to 8 minutes, the bleeding time in the mice treated with the heparin liposomes ranged from 21 to 25 minutes (except for one mouse in which that bleeding time was of 9 minutes).

In all the foregoing tests, the feeding of the animals was by deep repeated gastro-duodenal forced feeding.

It has also been found that a prolongation of the thrombin time was still increased in rats as compared to controls, 18 hours after they had received an injection of a heparin-containing-liposomes according to the invention. This shows the delayed action type which the heparin-containing liposomes of the invention are capable of inducing in vivo.

The heparin-containing-liposomes are useful like heparin for the control of blood coagulability, particularly for preventing hypercoagulabilities of the type which are encountered, for instance in patients suffering from vascular, veinous or thrombolitic diseases.

The use of heparin-containing liposomes is particularly desirable in heparin-based treatments involving its administration by routes other than parenteral, for example by oral or rectal routes, or also in the form of ointments, etc.

The invention also concerns the pharmaceutical compositions containing such heparin-containing-liposomes associated with pharmaceutical vehicles.

They particularly concern orally administrable compositions in a form permitting the liposomes containing heparin to cross the gastric barrier without damage. For instance the liposomes containing heparin are incorporated in gastro-resistant pharmaceutical compositions together with an appropriate vehicle for oral administration, enabling the active principle to be released in the duodenum only. Advantageously the heparin-containing-liposomes are formed into gastro-resistant capsules, for instance of the type manufactured by SHERER, with each capsule containing from 20 to 500 i.u. of heparin.

The liposomes containing heparin within their vesicles may also be put into suspension in an injectable vehicle. An advantageous example of a preparation, intended for continuous perfusion, comprises the final liposome product, prepared in a sterile manner, suspended in an isotonic solution and distributed in ampoules or flasks, in volumes of from 1 to 10 ml containing from 100 to 20 000 i.u. of heparin.

We claim:

1. A method for the control of blood coagulability in vivo comprising orally adminstering in an amount effective to control blood coagulation a pharmaceutical composition comprising orally administrable heparin-liposomes, the lipids of which are formed of non-toxic physiologically acceptable and metabolizable phospholipids, with heparin retained therein or thereon in association with a pharmaceutical vehicle.

2. A method for the control of blood coagulability in vivo comprising orally administering in an amount effective to control blood coagulation a pharmaceutical composition comprising orally administrable heparin-liposomes, the lipids of which comprise lecithin, with heparin retained therein or thereon in association with a pharmaceutical vehicle.

* * * * *